(12) United States Patent
Tadano et al.

(10) Patent No.: US 12,408,997 B2
(45) Date of Patent: Sep. 9, 2025

(54) FORCE SENSE NOTIFICATION DEVICE AND FORCE SENSE NOTIFICATION METHOD

(71) Applicant: RIVERFIELD Inc., Tokyo (JP)

(72) Inventors: Kotaro Tadano, Tokyo (JP); Yasushi Tanaka, Tokyo (JP); Teruyuki Nishihara, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 88 days.

(21) Appl. No.: 18/472,322

(22) Filed: Sep. 22, 2023

(65) Prior Publication Data

US 2024/0008937 A1   Jan. 11, 2024

Related U.S. Application Data

(63) Continuation of application No. PCT/JP2021/012009, filed on Mar. 23, 2021.

(51) Int. Cl.
*A61B 34/37* (2016.01)
*A61B 34/00* (2016.01)
*G08B 21/18* (2006.01)
*A61B 34/30* (2016.01)
*A61B 90/00* (2016.01)
*G08B 3/00* (2006.01)

(52) U.S. Cl.
CPC .............. *A61B 34/25* (2016.02); *A61B 34/37* (2016.02); *G08B 21/18* (2013.01); *A61B 2034/302* (2016.02); *A61B 2090/064* (2016.02); *G08B 3/00* (2013.01)

(58) Field of Classification Search
CPC .................................................... A61B 34/25
See application file for complete search history.

(56) References Cited

U.S. PATENT DOCUMENTS

| | | | | |
|---|---|---|---|---|
| 6,193,129 | B1* | 2/2001 | Bittner | A61B 17/1114 227/19 |
| 8,384,551 | B2* | 2/2013 | Ross | A61B 5/6831 600/595 |
| 2006/0241415 | A1 | 10/2006 | Boese et al. | |
| 2009/0030437 | A1* | 1/2009 | Houser | A61B 18/1442 422/1 |
| 2009/0299439 | A1* | 12/2009 | Mire | A61B 17/1671 606/53 |
| 2014/0052150 | A1* | 2/2014 | Taylor | G16H 20/40 606/130 |
| 2016/0148481 | A1* | 5/2016 | Althaher | A61B 5/4561 340/573.7 |
| 2018/0238883 | A1* | 8/2018 | Penny | B25J 9/14 |
| 2019/0090929 | A1 | 3/2019 | Brannan | |
| 2021/0282862 | A1* | 9/2021 | Bourlion | A61B 34/10 |

(Continued)

FOREIGN PATENT DOCUMENTS

| | | |
|---|---|---|
| CN | 103068348 A | 4/2013 |
| CN | 211409357 U | 9/2020 |

(Continued)

*Primary Examiner* — Travis R Hunnings
(74) *Attorney, Agent, or Firm* — Sughrue Mion, PLLC (57) ABSTRACT

A force sense notification device includes a speaker and a control device that receives a measurement signal indicating a magnitude of a force exerted on a surgical instrument, generates sound information based on the magnitude of the force, and outputs the sound information through the speaker.

16 Claims, 4 Drawing Sheets

(56) References Cited

U.S. PATENT DOCUMENTS

2022/0151721 A1    5/2022  Haraguchi et al.
2022/0297598 A1    9/2022  Hattori et al.
2023/0338107 A1*  10/2023  Nicholas ............ A61B 17/1155

FOREIGN PATENT DOCUMENTS

| JP | 2020-146374 A | 9/2020 |
|----|---------------|--------|
| WO | 2021/033607 A1 | 2/2021 |

* cited by examiner

FORCE SENSE NOTIFICATION DEVICE AND FORCE SENSE NOTIFICATION METHOD

CROSS-REFERENCE TO RELATED APPLICATION

This Application is a continuation of International Application No. PCT/JP2021/012009, filed Mar. 23, 2021 in the Japan Patent Office, the contents of which being herein incorporated by reference in its entirety.

BACKGROUND

The present disclosure relates to a force sense notification device and a force sense notification method, which are used in a surgery assistance robot system.

In endoscopic surgery using a surgery assistance robot system, a laparoscope, an endoscope, a forceps, or the like (hereinafter also referred to as a "surgical instrument") is used, and these surgical instruments are each attached to a surgery assistance robot for use.

A doctor and/or an operator of the endoscopic surgery (hereinafter also referred to as a "manipulator") manipulates the surgery assistance robot in the surgery assistance robot system, thus enabling a remote control of the surgical instrument via the surgery assistance robot. The surgery assistance robot system may enable more intuitive manipulation of the surgical instrument and may, in some cases, provide force feedback for conveying an external force acting on the surgical instrument to the doctor and/or operator.

SUMMARY

It is an aspect to provide a force sense notification device and a force sense notification method, capable of inhibiting false recognition of auditory information derived from force feedback.

According to an aspect of one or more embodiments, there is provided a force sense notification device comprising a control device configured to implement at least an input part which receives a measurement signal indicating a magnitude of an acting force exerted on a surgical instrument; a sound information generator configured to generate, based on the measurement signal, notification sound information indicating the magnitude of the acting force; and an outputter configured to output the notification sound information generated by the sound information generator to a sound generator configured to emit a sound based on the notification sound information.

According to another aspect of one or more embodiments, there is provided a force sense notification method comprising receiving a measurement signal indicating a magnitude of an acting force exerted on a surgical instrument; generating, based on the measurement signal, notification sound information indicating the magnitude of the acting force; and outputting the notification sound information to a sound generator configured to emit a sound based on the notification sound information.

According to yet another aspect of one or more embodiments, there is provided a force sense notification device comprising a speaker; and a control device configured to receive a measurement signal indicating a magnitude of a force exerted on a surgical instrument, generate sound information based on the magnitude of the force, and output the sound information through the speaker.

BRIEF DESCRIPTION OF THE DRAWINGS

The above and/or other aspects will become apparent from the following description of various embodiments and with reference to the following drawings, in which.

DETAILED DESCRIPTION

The force feedback function is an effective and important function for the manipulator (e.g., the doctor and/or operator) to improve the quality and safety of the surgery. Examples of force feedback functions include a function using tactile information provided from an operation part as a haptic device, and a function using visual information provided from a display device.

The tactile sensation is duller than the other sensations and thus may be unsuitable for conveying highly accurate information to the manipulator via the tactile sensation of the manipulator. In contrast, when the visual sensation is used, highly accurate information may be able to be conveyed as compared with cases where the other sensations are used. On the other hand, when the manipulator keeps a close watch on the surgery screen in the surgery assistance robot system, there is concern that the visual information separately displayed via the force feedback function may be overlooked by the manipulator.

In addition to the force feedback function using the tactile information or the visual information as described above, a force feedback function using auditory information provided from a sound generating device may be concurrently used.

However, in an operating room where the surgery assistance robot system is used, irrelevant sounds (hereinafter also referred to as "noise") different from the auditory information derived from the force feedback function, such as alarm tones from a biological information monitor and/or alarm tones from various other medical devices, may be generated commonly. In this case, there are possibilities that the manipulator falsely recognizes the noise as the above-described auditory information derived from the force feedback function, and/or that the manipulator falsely recognizes the auditory information as the noise.

It is one aspect to provide a force sense notification device and a force sense notification method, capable of inhibiting false recognition of auditory information derived from force feedback.

A force sense notification device according to some embodiments may include a device configured to notify a manipulator, in a perceptible manner, of a magnitude of an acting force exerted on a surgical instrument used in surgery. The force sense notification device comprises a signal input part, a sound information generator, and a notification sound outputter. A measurement signal indicating the magnitude of the acting force exerted on the surgical instrument is input to the signal input part. The sound information generator is configured to generate, based on the measurement signal, notification sound information indicating the magnitude of the acting force using at least a first notification sound and a second notification sound. The first notification sound contains at least a first low-pitched note and a first high-pitched note that is pitched higher than the first low-pitched note and that is consonant with the first low-pitched note. The second notification sound contains at least a second low-pitched note and a second high-pitched note that is pitched higher than the second low-pitched note and that is consonant with the second low-pitched note. At least one of the second low-pitched note or the second high-pitched note is different in pitch from the first low-pitched note and the first high-pitched note. The notification sound outputter is configured to output the notification sound information generated by the sound information generator to a sound generator configured to generate a sound based on the notification sound information.

A force sense notification method according to some embodiments may include a method for notifying a manipulator, in a perceptible manner, of a magnitude of an acting force exerted on a surgical instrument used in surgery. The force sense notification method comprises a signal input step, a sound information generation step, and a notification sound output step. The signal input step is for inputting a measurement signal for the magnitude of the acting force exerted on the surgical instrument. The sound information generation step is for generating, based on the measurement signal, notification sound information indicating the magnitude of the acting force using at least a first notification sound and a second notification sound. The first notification sound contains at least a first low-pitched note and a first high-pitched note that is pitched higher than the first low-pitched note and that is consonant with the first low-pitched note. The second notification sound contains at least a second low-pitched note and a second high-pitched note that is pitched higher than the second low-pitched note and that is consonant with the second low-pitched note. At least one of the second low-pitched note or the second high-pitched note is different from the first low-pitched note and the first high-pitched note. The notification sound output step is for outputting the generated notification sound information to a sound generator configured to generate a sound based on the notification sound information.

According to the force sense notification device according to some embodiments, the first notification sound or the second notification sound, each containing the notes that are different in pitch and that are consonant with each other, is emitted according to the magnitude of the acting force exerted on the surgical instrument. For example, when the magnitude of the acting force is smaller, the first notification sound is emitted, and when the magnitude of the acting force is larger, the second notification sound is emitted.

Since the first notification sound and the second notification sound contain the notes with different pitches, it is easier to make a distinction from, for example, a sound formed of a note with a single pitch and emitted from another device.

In some embodiments, the first high-pitched note may be consonant with the first low-pitched note.

According to such a configuration, the first notification sound contains the notes consonant with each other, thus making it less likely to give an unpleasant impression to those who hear the first notification sound. This makes it possible to inhibit an adverse effect on the manipulator's concentration on the surgery.

In some embodiments, the second high-pitched note may be consonant with the second low-pitched note.

According to such a configuration, the second notification sound contains the notes consonant with each other, thus making it less likely to give an unpleasant impression to those who hear the second notification sound. This makes it possible to inhibit an adverse effect on the manipulator's concentration on the surgery.

In some embodiments, at least one of the first notification sound or the second notification sound may contain three or more notes different in pitch from each other and that the three or more notes different in pitch are notes pitched to be consonant with each other.

According to such a configuration, the notes contained in at least one of the first notification sound or the second notification sound are consonant with each other, thus making it less likely to give an unpleasant impression to those who hear the first notification sound and the second notification sound.

In some embodiments, the second low-pitched note may be pitched higher than the first low-pitched note and the second high-pitched note may be pitched higher than the first high-pitched note.

By setting the second low-pitched note to be pitched higher than the first low-pitched note and setting the second high-pitched note to be pitched higher than the first high-pitched note as described above, it becomes easier for those who hear the notification sounds to make a distinction between the first notification sound and the second notification sound.

In some embodiments, the first low-pitched note and the second low-pitched note may be repeatedly changed in loudness or the first high-pitched note and the second high-pitched note may be repeatedly change in loudness.

By repeatedly changing the loudness of one of the notes contained in the first notification sound and the second notification sound, it becomes easier for those who hear the notification sounds to make a distinction between a sound emitted from another device and the first notification sound or the second notification sound.

In some embodiments, a pace of repeated changes in the loudness of the second notification sound may be different from a pace of repeated changes in the loudness of the first notification sound.

By setting the paces of the repeated changes in the loudness to be different between the first notification sound and the second notification sound as described above, it becomes easier for those who hear the notification sounds to make a distinction between the first notification sound and the second notification sound.

In some embodiments, the first high-pitched note and the second high-pitched note may be notes a seventh above the first low-pitched note and the second low-pitched note, respectively.

By setting the high-pitched notes to the notes a seventh above the low-pitched notes as described above, a neutral impression is likely to be given to those who hear the first notification sound and the second notification sound. This makes it less likely to have an adverse effect, such as disturbing the concentration, as compared with a notification sound that gives a gloomy impression and a notification sound that gives a cheerful impression, for example.

In some embodiments, the sound information generator is configured to, when the magnitude of the acting force is larger than or equal to a specified threshold, generate the notification information indicating that the magnitude of the acting force is larger than or equal to the specified threshold using a third notification sound different from the first notification sound and the second notification sound.

By using the third notification sound to indicate that the magnitude of the acting force is larger than or equal to the specified threshold as described above, it is easier to convey that the magnitude of the acting force has become larger than or equal to the specified threshold as compared with a case where the third notification sound is not used.

In some embodiments, the third notification sound contains a third low-pitched note and a third high-pitched note pitched higher than the third low-pitched note and that the third low-pitched note and the third high-pitched note are dissonant with each other.

By using the third notification sound containing the third low-pitched note and the third high-pitched note, which are dissonant with each other, as described above, it is likely for those who hear the third notification sound to have an unpleasant impression. This makes it easier for those who hear the notification sounds to notice the third notification sound when the third notification sound is emitted.

In some embodiments, the third notification sound may contain at least a third low-pitched note, a third middle-pitched note pitched higher than the third low-pitched note, and a third high-pitched note pitched higher than the third middle-pitched note. In some embodiments, one note of the third low-pitched note, the third middle-pitched note, and the third high-pitched note may be emitted continuously and remaining two notes are emitted alternately.

In such a mode in which one note of the third low-pitched note, the third middle-pitched note, and the third high-pitched note in the third notification sound is emitted continuously and the remaining two notes are emitted alternately, it is likely for those who hear the third notification sound to have an unpleasant impression. This makes it easier for those who hear the notification sounds to notice the third notification sound when the third notification sound is emitted.

In some embodiments, a switcher configured to switch permission of generation of a sound in the sound generator and prohibition (or stop) of the generation may be provided.

By providing the switcher as described above, it becomes possible to choose permission of generation of a sound or prohibition (or stop) of generation of a sound, in the sound generator. The switcher may control operation of the sound generator, may control output of the notification sound information to the sound generator, or may control generation of the notification sound information.

According to the force sense notification device and the force sense notification method of various embodiments, the first notification sound or the second notification sound each containing the notes with different pitches is emitted according to the magnitude of the acting force exerted on the surgical instrument. This results in producing an effect that false recognition of the auditory information relating to force feedback can be inhibited.

A surgery assistance robot system 1 according to some embodiments will be described below with reference to FIGS. 1 to 4. The surgery assistance robot system 1 according to various embodiments is used for surgery assistance, and is suitable for assisting endoscopic surgery, for example.

Figure 1:
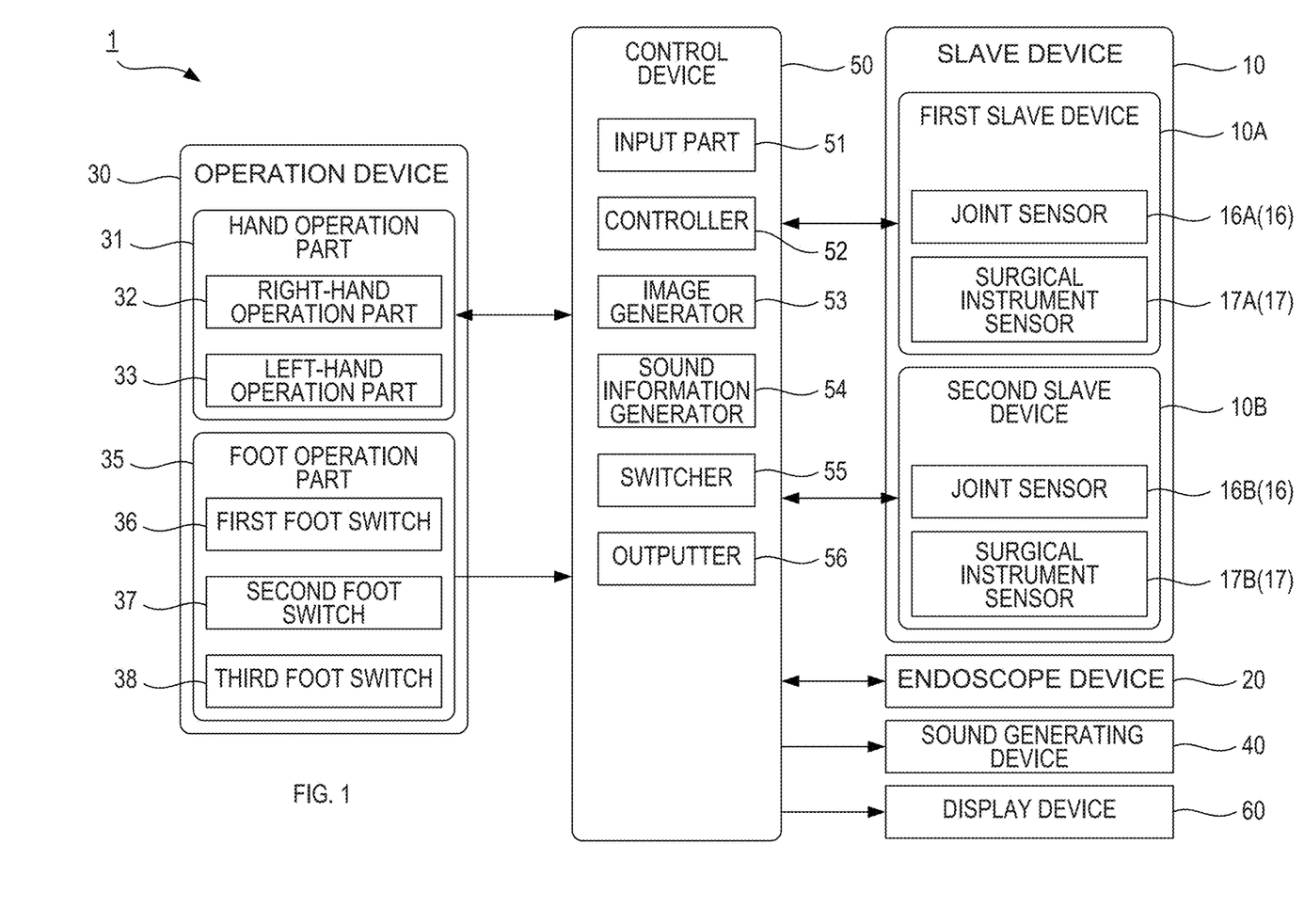
FIG. 1 is a block diagram explaining a configuration of a surgery assistance robot system according to some embodiments.

As shown in FIG. 1, the surgery assistance robot system 1 may comprise a slave device 10, an endoscope device 20, an operation device 30, a sound generating device 40, a control device 50, and a display device 60. The sound generating device 40 corresponds to one example of a sound generator. In some embodiments, the sound generating device 40 may be a speaker.

Figure 2:
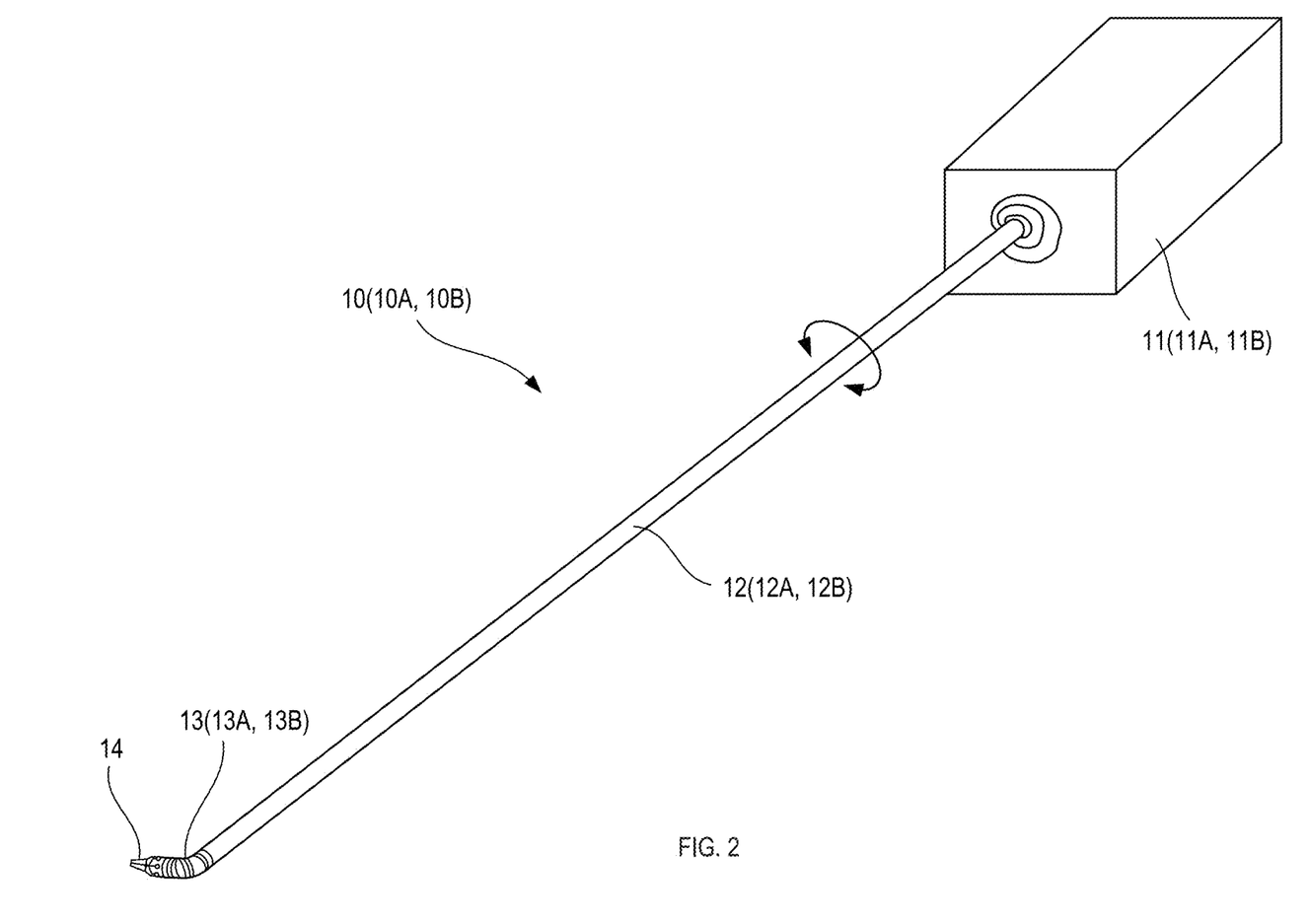
FIG. 2 is a perspective view explaining a configuration of a slave device, according to some embodiments.

As shown in FIG. 2, the slave device 10 supports a surgical instrument 14. In one example, the surgical instrument 14 may be a forceps for use in endoscopic surgery. The slave device 10 controls at least one of a position or an attitude of the surgical instrument 14 in accordance with an operation state of the operation device 30. In a case where the surgical instrument 14 is a forceps, the slave device 10 drives the forceps to open and close. In some embodiments, the slave device 10 may drive the forceps to turn, rotate, and/or twist.

The slave device 10 may comprise a first slave device 10A and a second slave device 10B. The number of the slave devices that the slave device 10 comprises may be more than two, or may be one.

The first slave device 10A and the second slave device 10B may be robot arms. In some embodiments, the first slave device 10A and the second slave device 10B may have the same configuration and each may support a corresponding surgical instrument 14 of the same kind.

It is sufficient for the first slave device 10A and the second slave device 10B to be devices to control at least one of the position or the attitude of the surgical instrument 14 and, when the surgical instrument 14 is a forceps, it is sufficient to be devices capable of driving the forceps to open and close; thus, there is no need to have an arm-like configuration.

As shown in FIG. 2, the first slave device 10A and the second slave device 10B ay each comprise a cartridge 11, a shaft 12, and a joint part 13. As for the cartridge 11, the shaft 12, and the joint part 13, when it is not necessary to distinguish whether the cartridge 11, the shaft 12, and the joint part 13 are those provided for the first slave device 10A or those provided for the second slave device 10B, the cartridge 11, the shaft 12, and the joint part 13 are referred to as the cartridge 11, the shaft 12, and the joint part 13, respectively. When it is to be distinguished whether the cartridge 11, the shaft 12, and the joint part 13 are those provided for the first slave device 10A or those provided for the second slave device 10B, the cartridge 11, the shaft 12, and the joint part 13 are distinguished by being accordingly referred to as a cartridge 11A, a shaft 12A, and a joint part 13A, respectively, or referred to as a cartridge 11B, a shaft 12B, and a joint part 13B, respectively.

The cartridge 11 supports the shaft 12, the joint part 13, and the surgical instrument 14. In some embodiments, the cartridge 11 is formed in a cuboidal shape.

The cartridge 11 may house a drive source, such as a pneumatic actuator, to drive at least one of the shaft 12, the joint part 13, or the surgical instrument 14. The cartridge 11 may also house at least one of a joint sensor 16 (see FIG. 1) to measure an external force applied to the joint part 13, or a surgical instrument sensor 17 (see FIG. 1) to measure an opening/closing force applied externally by the forceps as the surgical instrument 14. The external force applied to the joint part 13 and the opening/closing force applied externally by the forceps as the surgical instrument 14 each correspond to one example of an acting force.

As for the joint sensor 16 and the surgical instrument sensor 17, when it is not necessary to distinguish whether they are those provided to the first slave device 10A or those provided to the second slave device 10B, they are referred to as the joint sensor 16 and the surgical instrument sensor 17, respectively. When it is to be distinguished whether they are those provided to the first slave device 10A or those provided to the second slave device 10B, they are distinguished by being accordingly referred to as a joint sensor 16A and a surgical instrument sensor 17A, respectively, or referred to as a joint sensor 16B and a surgical instrument sensor 17B, respectively.

The shaft 12 is a member formed in a circular-cylindrical or circular-columnar shape, extending from the cartridge 11. The shaft 12 is configured to be rotatable about its central axis with respect to the cartridge 11. The shaft 12 may be formed in a polygonal-cylindrical or prismatic shape.

The joint part 13 supports the surgical instrument 14, and also controls the position and/or the attitude of the surgical instrument 14 by being bent. The joint part 13 is located between the shaft 12 and the surgical instrument 14. In other words, a first end of the joint part 13 is connected to an end, of the two ends of the shaft 12, on the side farther from the cartridge 11, and a second end of the joint part 13 is connected to the surgical instrument 14. A configuration of the joint part 13 that may be employed is any configuration that allows it to be bent. A specific configuration of the joint part 13 is not particularly limited.

The endoscope device 20 acquires video or images captured during endoscopic surgery. Specifically, the endoscope device 20 acquires video or images of an area that is within the patient's body cavity and that is the subject of the surgery. Information of the acquired video or images is output to the control device 50. A configuration of the endoscope device 20 may be any configuration that can acquire the video or images and output the information thereof, and the configuration is not particularly limited.

The operation device 30 is used to control the slave device 10. Specifically, the operation device 30 is used when operating the slave device 10 to perform endoscopic surgery. The operation device 30 is also referred to as a master unit.

The operation device 30 may include a hand operation part 31 and a foot operation part 35. The hand operation part 31 is used when a manipulator of the surgery assistance robot system 1 (e.g., a doctor or an operator of the endoscopic surgery) inputs movement of the slave device 10 by hand.

The hand operation part 31 may include a right-hand operation part 32 and a left-hand operation part 33 corresponding respectively to a right hand and a left hand of the manipulator. The right-hand operation part 32 and the left-hand operation part 33 convert operation information input by the manipulator into a signal and output the signal to a controller 52. Moreover, the right-hand operation part 32 and the left-hand operation part 33 present a force sense to the manipulator based on a control signal input from the controller 52. "Present a force sense" as described here refers to conveying information on a force acting on the slave device 10 to the manipulator so that the manipulator can perceive that the force is acting on the slave device 10. When the force sense is presented to the manipulator through the hand operation part 31, the information may be conveyed via the tactile sensation of the manipulator's finger. As a method of presenting the force sense, the information may be conveyed via the visual sensation, the auditory sensation, or the like, as well as conveying the information via the tactile sensation.

The right-hand operation part 32 and the left-hand operation part 33 are not limited in terms of the configuration and system. In some embodiments, the hand operation part 31 may comprise both the right-hand operation part 32 and the left-hand operation part 33 as described above, or in some embodiments may comprise only one of the right-hand operation part 32 and the left-hand operation part 33.

The foot operation part 35 is provided so as to enable the manipulator to cause the slave device 10 to operate and to cause the slave device 10 to fulfill its function with his/her foot. The foot operation part 35 may include a first foot switch 36, a second foot switch 37, and a third foot switch 38. The first foot switch 36, the second foot switch 37, and the third foot switch 38 are switches operated by being stepped on by the manipulator with his/her foot.

Illustrative examples of the functions fulfilled by operation of the foot operation part 35 may include supplying the surgical instrument 14 with high frequency current and stopping the current, switching a control mode of the slave device 10, and so forth. A type and details of operation by the foot operation part 35 are not limited. According to various embodiments, the foot operation part 35 may comprise three foot switches as described above, may comprise less than three foot switches, or may comprise more than three foot switches.

The sound generating device 40 generates sound based on the signal input from the control device 50. This configuration enables at least some of the persons involved in the endoscopic surgery, including the manipulator, to perceive the sound emitted from the sound generating device 40. A configuration and the like to generate the sound are not particularly limited. The signal input from the control device 50 corresponds to one example of notification sound information.

The control device 50 controls operation of the slave device 10, sound generation by the sound generating device 40, display contents and display modes in the display device 60, and so forth.

The control device 50 may be an information processor, such as a computer. Specifically, as shown in FIG. 1, the control device 50 may include a CPU, a ROM, a RAM, an input/output interface, and so forth. CPU is an abbreviation for a central processing unit. A program stored in a storage device, such as the above-described ROM, when accessed and executed, causes the CPU, the ROM, the RAM, and the input/output interface to cooperate to function at least as an input part 51, the controller 52, an image generator 53, a sound information generator 54, a switcher 55, and an outputter 56. The input part 51 corresponds to one example of a signal input part. The outputter 56 corresponds to one example of a notification sound outputter.

The input part 51 is an interface that connects the external devices to the control device 50 so as to allow input of the signals from the external devices to the control device 50. Specifically, the input part 51 is connected to the operation device 30 so as to allow input of the signal including information on details of operation by the operation device 30 to the control device 50 from the operation device 30. Moreover, the input part 51 is connected to the endoscope device 20 so as to allow input of a signal indicating the video and/or images acquired by the endoscope device 20 to the control device 50 from the endoscope device 20.

In order to allow input to the control device 50 of a measurement signal from the joint sensor 16 that measures the external force applied to the joint part 13 and of a measurement signal from the surgical instrument sensor 17 that measures the opening/closing force applied externally by the forceps as the surgical instrument 14, the input part 51 is connected to the joint sensor 16 and to the surgical instrument sensor 17, respectively.

Positions where the joint sensor 16 and the surgical instrument sensor 17 are arranged may be any positions that enable measurement of the external forces of respective measurement targets, and the positions are not particularly limited. Also, methods of measuring the external forces by the joint sensor 16 and the surgical instrument sensor 17 are not particularly limited.

The controller 52 generates a control signal for controlling operation of the slave device 10 and the surgical instrument 14 and a control signal for controlling fulfilment of the functions. The control signals are generated based on the signal that is input to the control device 50 from the operation device 30 and that includes the information on the details of the operation by the operation device 30.

The image generator 53 generates image information, which is information on video and/or images to be displayed on the display device 60. Specifically, the image generator 53 generates the image information based on the signal for the video and/or images input to the control device 50 from the endoscope device 20, and on the signals input to the control device from the joint sensor 16 and the surgical instrument sensor 17. Details of the image information will be described below.

The sound information generator 54 generates notification sound information, which is information on sound to be generated in the sound generating device 40. Specifically, the sound information generator 54 generates the notification sound information based on the signals input to the control device 50 from the joint sensor 16 and the surgical instrument sensor 17. Details of the notification sound information will be described below.

The switcher 55 performs control to permit or prohibit generation of sound in the sound generating device 40. In other words, the switcher 55 controls ON/OFF of sound generation in the sound generating device 40. For example, ON/OFF of sound generation is controlled based on an instruction on ON/OFF of sound generation input by the manipulator of the surgery assistance robot system 1 or other persons.

The input of the instruction on ON/OFF of sound generation may be performed via a switch (not shown) or the like included in the control device 50, or may be performed via the foot operation part 35 of the operation device 30. A device for the input is not particularly limited.

The control of ON/OFF of sound generation may be performed by controlling operation of the sound generating device 40, or may be performed by controlling output of a signal from the control device 50 to the sound generating device 40, or may be performed by controlling generation of a signal to be output to the sound generating device 40.

The outputter 56 is an interface for externally outputting, from the control device 50, the control signal generated in the controller 52, a signal for the image information generated in the image generator 53, and a signal for the notification sound information generated in the sound information generator 54.

Specifically, the outputter 56 is connected to the slave device 10 and the surgical instrument 14 so that the control signals can be output from the control device 50 to the slave device 10 and the surgical instrument 14. In addition, the outputter 56 is connected to the display device 60 so that the image information can be output from the control device 50 to the display device 60, and is connected to the sound generating device 40 so that the notification sound information can be output from the control device 50 to the sound generating device 40.

The display device 60 displays the video and/or images based on the image information input from the control device 50. The display device 60 performs such display for the persons involved in the surgery, including the operator of the endoscopic surgery. In the display device 60, the method and configuration for displaying the video and/or images are not particularly limited.

Next, an explanation will be given of control in the surgery assistance robot system 1 having the above-described configuration, specifically, of control related to notification of a force sense. First, flow of an arithmetic processing in the control device 50 will be described with reference to FIG. 3, and then contents to be notified of will be described.

Figure 3:
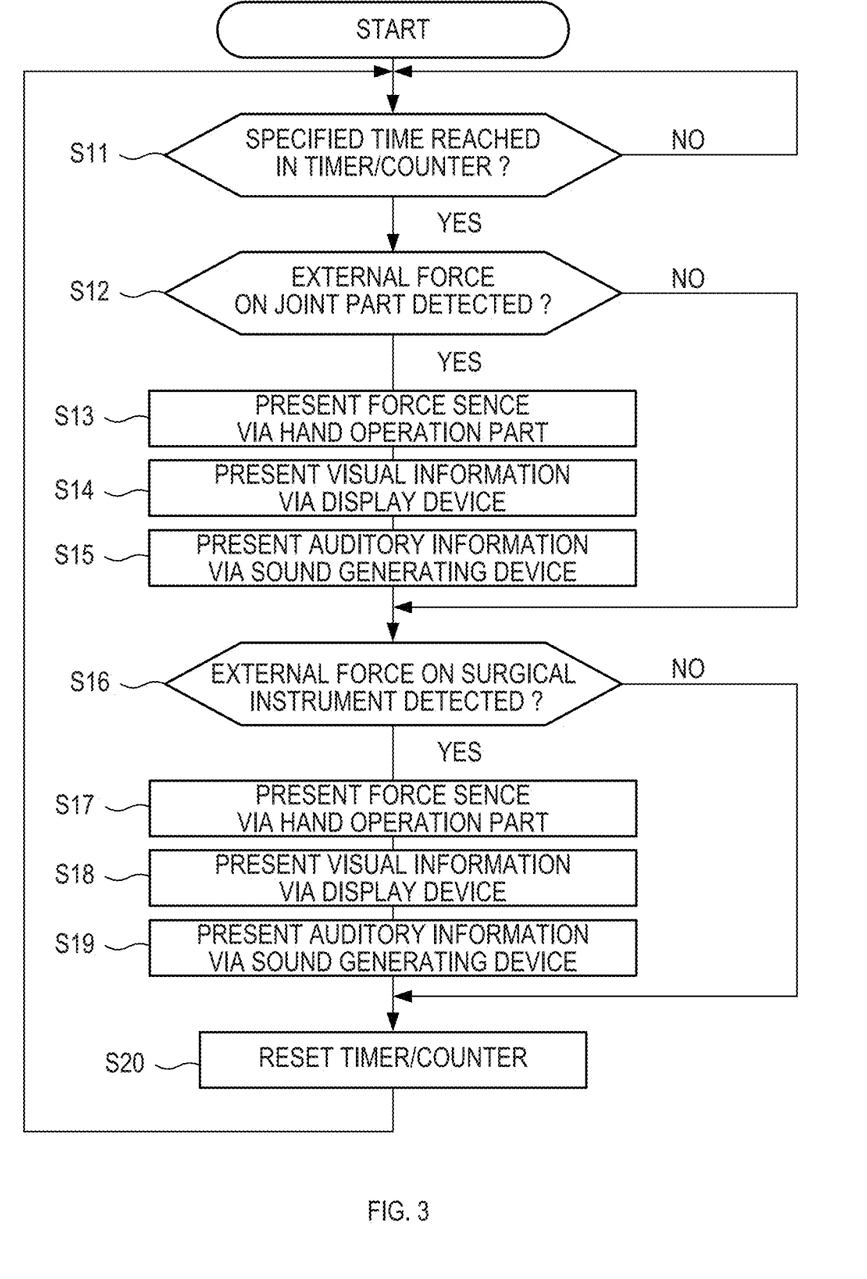
FIG. 3 is a flowchart explaining a control method of display of a force sense in a control device, according to some embodiments.

FIG. 3 is a flowchart explaining a control method of display of a force sense in a control device, according to some embodiments.

Upon supply of electric power to the control device 50, the arithmetic processing in the control device 50 is initiated, and the time from when the electric power is supplied is measured by a timer/counter. As shown in FIG. 3, the control device 50 performs a process to determine whether the time measured by the timer/counter has reached a specified time (S11). The specified time may be 200 ms, in one example. The specified time may be longer than or shorter than 200 ms, and may be set as appropriate in accordance with a required specification or another factor.

If it is determined that the time measured by the timer/counter has not reached the specified time (S11: NO), the control device 50 performs the determination process of S11 again.

If it is determined that the time measured by the timer/counter has reached the specified time (S11: YES), the control device 50 performs a process to determine whether an external force exerted on the joint part 13 has been detected (S12). In other words, the control device 50 determines whether a joint measurement signal, which is a measurement signal for the external force, has been input to the input part 51 from the joint sensor 16. The process of S12 corresponds to one example of an input step.

If it is determined that the external force exerted on the joint part 13 has been detected (S12: YES), the control device 50 performs a process to cause the hand operation part 31 to present the detected external force as a force sense (S13). The magnitude of the external force is calculated by computation based on the measurement signal output from the joint sensor 16.

In the process of S13, the control device 50 performs a process to cause the hand operation part 31 corresponding to the slave device provided with the joint sensor 16 that has output the measurement signal to present the detected external force as a force sense. For example, when the joint sensor 16 that has output the measurement signal is a sensor that measures an external force acting on the shaft 12A of the first slave device 10A, the control device 50 performs a process to cause the hand operation part 31 (specifically, the right-hand operation part 32 or the left-hand operation part 33) used for operation of the first slave device to present the detected external force as a force sense.

Also, in S13, the control device 50 performs a process to set the strength of the force sense to be presented, in accordance with the magnitude of the external force calculated based on the measurement signal from the joint sensor 16. The corresponding hand operation part 31 presents, to the manipulator, the force sense corresponding to the external force acting on the corresponding slave device, based on the control signal input from the control device 50.

Upon completion of the process of S13, the control device 50 performs a process to present the detected external force as information that can be grasped through the visual sensation (S14). Specifically, the control device 50 performs a process to display the information indicating the external force on the display device 60 as visual information. First, the control device 50 generates the image information indicating the video and/or images corresponding to the magnitude of the external force calculated based on the measurement signal input from the joint sensor 16. Details of the process to generate the image information will be described below. The generated image information is output to the display device 60. The display device 60 displays the video and/or images based on the input image information.

Upon completion of the process of S14, the control device 50 performs a process to present the detected external force as information that can be grasped through the auditory sensation (S15). Specifically, the control device 50 performs a process to cause the information indicating the external force to be output from the sound generating device 40 as auditory information. The process of S15 corresponds to one example of a sound information generation step and an output step. In S15, the control device 50 generates the notification sound information indicating the sound corresponding to the magnitude of the external force calculated based on the measurement signal input from the joint sensor 16. Details of the process to generate the notification sound information will be described below. The generated notification sound information is output to the sound generating device 40. The sound generating device 40 emits sound based on the input notification sound information.

Upon completion of the process of S15, or if an external force exerted on the joint part 13 has not been detected in S12 (S12: NO), the control device 50 performs a process to determine whether an external force exerted on the surgical instrument 14 has been detected (S16). In other words, the control device 50 performs a process to determine whether a surgical instrument measurement signal, which is a measurement signal for the external force, has been input to the input part 51 from the surgical instrument sensor 17. The process of S16 corresponds to one example of an input step.

In the process of S16, if it is determined that the external force exerted on the surgical instrument 14 has been detected (S16: YES), the control device 50 performs a process to generate a control signal for presenting the detected external force as a force sense (S17). The detected external force is the magnitude of the external force measured by the surgical instrument sensor 17 (specifically, a force with which the forceps grasps or peels off the object). The detection of the external force is performed by calculation based on the measurement signal output from the surgical instrument sensor 17.

Specifically, in S17, the control device 50 performs a process to cause the hand operation part 31 corresponding to the slave device provided with the surgical instrument sensor 17 that has output the measurement signal to present the detected external force as a force sense. In addition, the control device 50 performs a process to set the strength of the force sense to be presented, in accordance with the magnitude of the external force calculated based on the input measurement signal. The corresponding hand operation part 31 presents, to the manipulator, the force sense corresponding to the external force acting on the corresponding surgical instrument sensor 17, based on the control signal output from the control device 50.

Upon completion of the process of S17, the control device 50 performs a process to present the detected external force as information that can be grasped through the visual sensation (S18). First, the control device 50 generates the image information indicating video and/or images corresponding to the magnitude of the external force calculated based on the measurement signal input from the surgical instrument sensor 17. Details of the process to generate the image information will be described below. The generated image information is output to the display device 60. The display device 60 displays the video and/or images based on the input image information.

Upon completion of the process of S18, the control device 50 performs a process to present the detected external force as information that can be grasped through the auditory sensation (S19). S19 corresponds to one example of a sound information generation step and an output step. First, the control device 50 generates the notification sound information indicating the sound corresponding to the magnitude of the external force calculated based on the measurement signal input from the surgical instrument sensor 17. Details of the process to generate the notification sound information will be described below. The generated notification sound information is output to the sound generating device 40. The sound generating device emits sound based on the input notification sound information.

Upon completion of the process of S19 or if it is determined that the external force exerted on the surgical instrument 14 has not been detected (S16: NO), the control device performs a process to reset the timer/counter to zero (S20). Upon completion of the process of such reset, the control device 50 returns to S11, and repeatedly performs the above-described processes. For example, the above-described processes are repeatedly performed at least during a period in which assistance for the endoscopic surgery by the surgery assistance robot system 1 is performed.

Next, the image information generated by the image generator 53 will be described.

Figure 4:
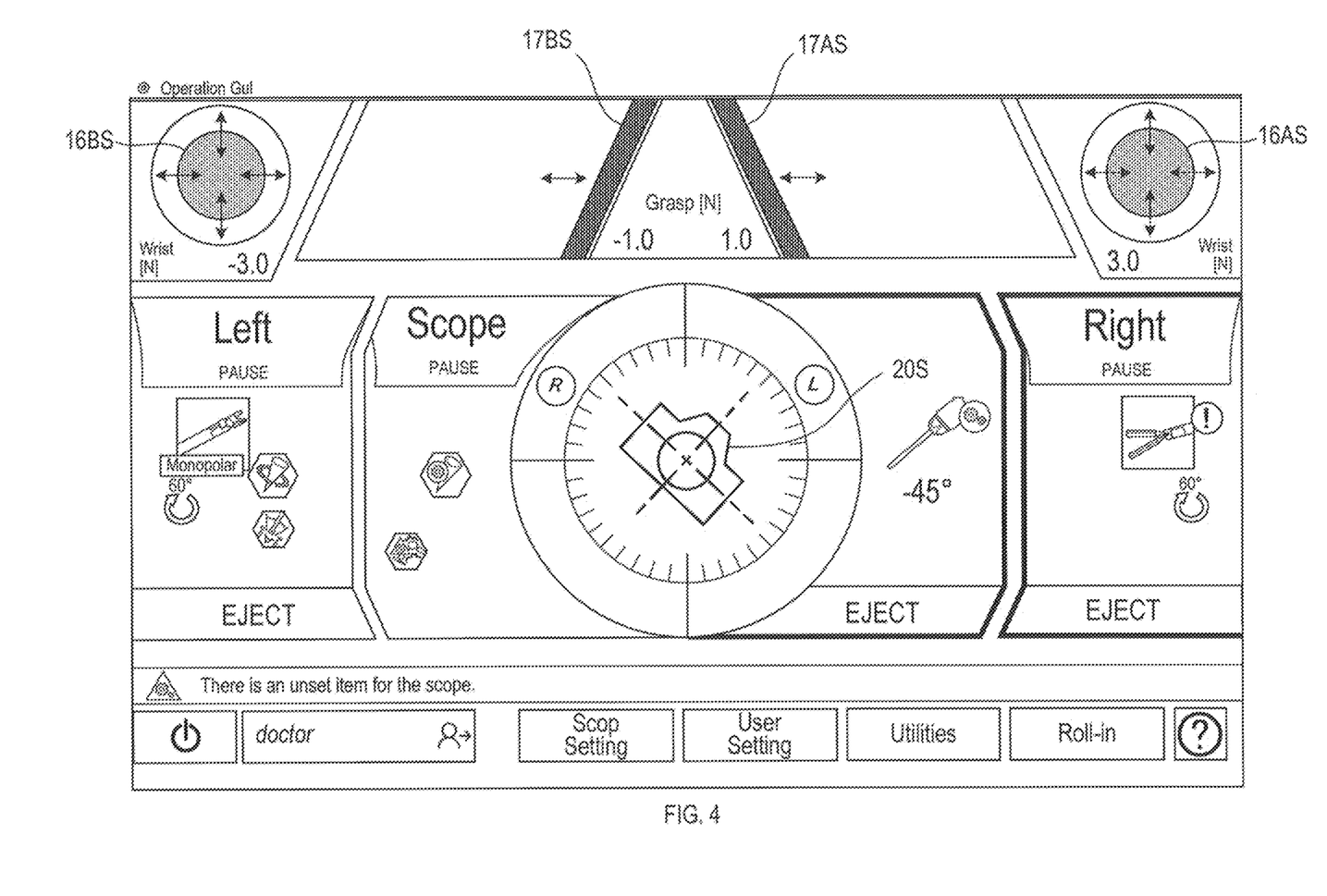
FIG. 4 is a schematic diagram explaining a mode of display in a display device, according to some embodiments.

FIG. 4 is a schematic diagram explaining a mode of display in a display device, according to some embodiments. Specifically, a mode of display in the display device 60 will be described. FIG. 4 is a schematic diagram explaining the mode of the images displayed by the display device 60 based on the image information generated by the image generator 53.

The video or images acquired by the endoscope device 20 may be displayed on a display separate from the display device 60, or may be displayed in an area, within a display area of the display device 60, different from an area where the images shown in FIG. 4 are displayed.

The image generator 53 generates the image information to be presented in specified display areas on a display surface of the display device 60. The image information is generated by the image generator 53 based on the signals input to the control device 50 from the joint sensor 16 and the surgical instrument sensor 17.

In the center of a middle section of the display area, information on the endoscope device 20 is displayed. For example, a FIG. 20S with a camera-like shape is displayed that indicates the inclination of the video or images acquired by the endoscope device 20.

Performed in the right half of an upper section of the display area is a display based on the signals input from the joint sensor 16 and the surgical instrument sensor 17 of the corresponding slave device 10, for example the first slave device 10A, arranged on the right side of the surgery assistance robot system 1.

Performed in the left half of the upper section of the display area is a display based on the signals input from the joint sensor 16 and the surgical instrument sensor 17 of the corresponding slave device 10, for example the second slave device 10B, arranged on the left side of the surgery assistance robot system 1.

Next, an explanation will be given of a display mode in presenting, as a force sense, the external force detected by each joint sensor 16 corresponding to the first slave device 10A or the second slave device 10B. The display mode in presenting the external force detected by the joint sensor 16 of the first slave device 10A as a force sense and the display mode in presenting the external force detected by the joint sensor 16 of the second slave device 10B as a force sense are the same as each other.

The external force detected by the joint sensor 16 of the first slave device 10A is presented on the right side of the right half of the upper section of the display area, as a force sense-representing FIG. 16AS having a circular shape. The external force detected by the joint sensor 16 of the second slave device 10B is presented on the left side of the left half of the upper section of the display area, as a force sense-representing FIG. 16BS having a circular shape.

For example, as the value of the external force detected by each joint sensor 16 becomes larger, the diameter of the corresponding force sense-representing FIG. 16AS or force sense-representing FIG. 16BS becomes larger (see arrows illustrated in FIG. 4). In contrast, as the value of the external force detected by each joint sensor 16 becomes smaller, the diameter of the corresponding force sense-representing FIG. 16AS or force sense-representing FIG. 16BS becomes smaller.

Next, an explanation will be given of a display mode in presenting, as a force sense, the external force detected by each surgical instrument sensor 17 corresponding to the first slave device 10A or the second slave device 10B. The display mode in presenting the external force detected by the surgical instrument sensor 17 of the first slave device 10A as a force sense and the display mode in presenting the external force detected by the surgical instrument sensor 17 of the second slave device 10B as a force sense are the same as each other.

The external force detected by the surgical instrument sensor 17 of the first slave device 10A is presented on the left side of the right half of the upper section of the display area, in other words on the side close to the center of the upper section, of the right half thereof, as a force sense-representing FIG. 17AS having a parallelogram shape. The external force detected by the surgical instrument sensor 17 of the second slave device 10B is presented on the right side of the left half of the upper section of the display area, in other words on the side close to the center of the upper section, of the left half thereof, as a force sense-representing FIG. 17B S having a parallelogram shape.

For example, as the value of the external force detected by each surgical instrument sensor 17 becomes larger, the length of the corresponding force sense-representing FIG. 17AS or force sense-representing FIG. 17BS in the left-right direction becomes larger (see arrows illustrated in FIG. 4). Specifically, the force sense-representing FIG. 17AS and the force sense-representing FIG. 17BS expand in the left-right direction from the center of the display surface.

In contrast, as the value of the external force detected by each surgical instrument sensor 17 becomes smaller, the length of the corresponding force sense-representing FIG. 17AS or force sense-representing FIG. 17B S in the left-right direction becomes smaller. Specifically, the force sense-representing FIG. 17AS and the force sense-representing FIG. 17BS contract toward the center of the display surface.

Next, an explanation will be given of the sound to be emitted from the sound generating device 40. Specifically, a mode of the sound to be emitted based on the notification sound information will be described. The sound information generator 54 generates the notification sound information, which is information indicating the sound to be emitted from the sound generating device 40. The notification sound information is generated by the sound information generator 54 based on the signals input from the joint sensor 16 and the surgical instrument sensor 17.

The sound information generator 54 performs a process to generate the notification sound information indicating the sound corresponding to the magnitude of the external force calculated based on the input measurement signals. The notification sound information includes at least one of information on a first notification sound, information on a second notification sound, or information on a third notification sound.

The notification sound information generated by the sound information generator 54 is input to the sound generating device 40 via the outputter 56. The sound generating device 40 emits at least one of the first notification sound, the second notification sound, or the third notification sound based on the input notification sound information.

The first notification sound, the second notification sound, and the third notification sound to be emitted based on the measurement signals from the joint sensor 16 and the surgical instrument sensor 17 of the first slave device 10A may be different from or may be the same as, in tone color, the first notification sound, the second notification sound, and the third notification sound to be emitted based on the measurement signals from the joint sensor 16 and the surgical instrument sensor 17 of the second slave device 10B. In the case where the first notification sound, the second notification sound, and the third notification sound are different in tone color, it is easier to identify whether the notification sound is that related to the first slave device 10A or that related to the second slave device 10B.

Similarly, the first notification sound, the second notification sound, and the third notification sound to be emitted based on the measurement signal from the joint sensor 16 may be different from or may be the same as, in tone color, the first notification sound, the second notification sound, and the third notification sound to be emitted based on the measurement signal from the surgical instrument sensor 17. In the case where the first notification sound, the second notification sound, and the third notification sound are different in tone color, it is easier to identify whether the notification sound is that related to the joint sensor 16 or that related to the surgical instrument sensor 17.

The first notification sound is a sound to be emitted when the calculated magnitude of the external force is less than a first threshold. In some embodiments, the first threshold may be set in advance. The first notification sound contains at least a first low-pitched note and a first high-pitched note that is pitched higher than the first low-pitched note and that is consonant with the first low-pitched note.

In some embodiments, the first notification sound may be a sound in which the first low-pitched note is the note C and the first high-pitched note is the note B. For example, the first notification sound may be a seventh chord. The first notification sound may be a seventh chord as mentioned now, or may be another chord, such as a triad. The first low-pitched note contained in the first notification sound and the first low-pitched note may have an interval forming a perfect consonance. Specifically, notes with an interval of a perfect fourth, a perfect fifth, or a perfect eighth may be used for the first notification sound. The first low-pitched note contained in the first notification sound and the first low-pitched note may have an interval forming an imperfect consonance. Specifically, notes with an interval of a minor second, a major second, a minor third, a major third, a minor sixth, a major sixth, a minor seventh, or a major seventh may be used for the first notification sound.

The second notification sound is a sound to be emitted when the calculated magnitude of the external force is larger than or equal to the first threshold and less than a second threshold. In some embodiments, the second threshold may be set in advance. Each of the first threshold and the second threshold corresponds to one example of a specified threshold. The second notification sound may contain at least a second low-pitched note and a second high-pitched note that is pitched higher than the second low-pitched note and that is consonant with the second low-pitched note. The second low-pitched note may be a note pitched higher than the first low-pitched note. The second high-pitched note may be a note pitched higher than the first high-pitched note.

In some embodiments, the second notification sound may be a sound in which the second low-pitched note is the note F and the second high-pitched note is the note E an octave higher. For example, the second notification sound is a seventh chord. The second notification sound may be a seventh chord as mentioned now, or may be another chord, such as a triad. The second low-pitched note contained in the second notification sound and the second low-pitched note may have an interval forming a perfect consonance. Specifically, notes with an interval of a perfect fourth, a perfect fifth, or a perfect eighth may be used for the second notification sound. The second low-pitched note contained in the second notification sound and the second low-pitched note may have an interval forming an imperfect consonance. Specifically, notes with an interval of a minor second, a major second, a minor third, a major third, a minor sixth, a major sixth, a minor seventh, or a major seventh may be used for the second notification sound.

The third notification sound is a sound to be emitted when the calculated magnitude of the external force is larger than or equal to the second threshold. In other words, the third notification sound is a sound to be emitted when the calculated magnitude of the external force is beyond the range anticipated in advance and an abnormality is considered to have occurred. The third notification sound may contain a third low-pitched note and a third high-pitched note pitched higher than the third low-pitched note. The third low-pitched note and the third high-pitched note may be dissonant with each other. In some embodiments, the third notification sound may be a dissonance.

The first threshold may be a threshold having a value smaller than that of the second threshold and may be a threshold related to switching between the first notification sound to be emitted when the calculated magnitude of the external force is relatively small and the second notification sound to be emitted when the calculated magnitude of the external force is relatively large. The first threshold may be a threshold whose value is set in advance, or may be a threshold whose value can be optionally set by the manipulator or another person.

According to the control device 50 and a force sense notification method configured as above, the first notification sound or the second notification sound, each containing the notes that are different in pitch and that are consonant with each other, may be emitted according to the magnitude of the external force exerted on the surgical instrument 14. Specifically, when the magnitude of the external force is smaller, the first notification sound is emitted, and when the magnitude of the external force is larger, the second notification sound is emitted.

The pitch of at least one of the second high-pitched note or the second low-pitched note contained in the second notification sound may be different from the pitches of the first high-pitched note and the first low-pitched note contained in the first notification sound. This configuration facilitates distinction from, for example, a sound formed of a note with a single pitch and emitted from another device. In other words, this configuration makes it easier to inhibit false recognition of the auditory information relating to force feedback.

Each of the first notification sound and the second notification sound may contain two or more notes consonant with each other. This configuration makes it less likely to give an unpleasant impression to those who hear the first notification sound and the second notification sound. In other words, this configuration makes it easier to inhibit an adverse effect on the manipulator's concentration.

At least one of the first notification sound or the second notification sound may contain two or more notes with different pitches, and the two or more notes with different pitches may be notes pitched to be consonant with each other. This configuration makes it less likely to give an unpleasant impression to those who hear the first notification sound and the second notification sound. In other words, this configuration makes it easier to inhibit an adverse effect on the manipulator's concentration.

By setting the second low-pitched note to be pitched higher than the first low-pitched note and setting the second high-pitched note to be pitched higher than the first high-pitched note, it becomes easier for those who hear the notification sounds to make a distinction between the first notification sound and the second notification sound.

By setting the first high-pitched note a seventh above the first low-pitched note and setting the second high-pitched note a seventh above the second low-pitched note, a neutral impression is likely to be given to those who hear the first notification sound and the second notification sound. This configuration makes it less likely to have an adverse effect, such as disturbing the manipulator's concentration, as compared with a notification sound that gives a gloomy impression and a notification sound that gives a cheerful impression, for example.

By using the third notification sound to indicate that the magnitude of the external force is larger than or equal to the second threshold, it becomes easier to convey that the magnitude of the external force has become larger than or equal to the second threshold as compared with a case where the third notification sound is not used.

By using the third notification sound containing the third low-pitched note and the third high-pitched note, which are dissonant with each other, it is likely for those who hear the third notification sound to have an unpleasant impression. This configuration makes it easier for those who hear the notification sounds to notice the third notification sound when the third notification sound is emitted.

By providing the switcher 55, it is possible to choose permission of generation of sound or prohibition (or stop) of generation of sound in the sound generating device 40. That is, the sound generating device 40 may be turned on or off. In other words, presence or absence of the force feedback through the auditory sensation can be chosen according to the manipulator's preference, thus facilitating inhibition of an adverse effect on the manipulator's concentration.

In some embodiments, each note contained in the first notification sound and the second notification sound may have a constant loudness. In some embodiments, at least one of one of the notes contained in the first notification sound or one of the notes contained in the second notification sound may be changed in loudness repeatedly (i.e., may be a vibrato). For example, a mode may be adopted in which the loudness of each of the first low-pitched note and the second low-pitched note is constant and the loudness of each of the first high-pitched note and the second high-pitched note changes repeatedly.

By repeatedly changing the loudness of one of the notes contained in the first notification sound and the second notification sound, it becomes easier for those who hear the notification sounds to make a distinction between a sound emitted from another device and the first notification sound or the second notification sound.

The paces of repeated changes in the loudness of the first notification sound and the second notification sound may be the same as or different from each other. For example, a mode may be adopted in which the pace of repeated changes in the loudness of the first notification sound is relatively slow and the pace of repeated changes in the loudness of the second notification sound is relatively rapid.

By setting the paces of the repeated changes in the loudness to be different between the first notification sound and the second notification sound, it becomes easier for those who hear the notification sounds to make a distinction between the first notification sound and the second notification sound. In this case, the pitches of the notes contained in the first notification sound and the second notification sound may be different from each other as described above, or may be the same as each other.

As described above, in some embodiments, the third notification sound may be a sound containing the third low-pitched note and the third high-pitched note dissonant with the third low-pitched note. In some embodiments, the third notification sound may be a sound containing at least the third low-pitched note, a third middle-pitched note pitched higher than the third low-pitched note, and the third high-pitched note pitched higher than the third middle-pitched note, in which one note of the third low-pitched note, the third middle-pitched note, and the third high-pitched note is emitted continuously and the remaining two notes are emitted alternately. For example, the third notification sound may be a sound in which the lower note C as the third low-pitched note is emitted continuously and the note B as the third middle-pitched note and the upper note C as the third high-pitched note are emitted alternately.

In such a mode in which one note of the third low-pitched note, the third middle-pitched note, and the third high-pitched note in the third notification sound is emitted continuously and the remaining two notes are emitted alternately, it is likely for those who hear the third notification sound to have an unpleasant impression. This configuration makes it easier for those who hear the notification sounds to notice the third notification sound when the third notification sound is emitted.

In some embodiments, the notification sound information may include at least one of the information on the first notification sound, the information on the second notification sound, or the information on the third notification sound. Further, the sound generating device 40 may emit at least one of the first notification sound, the second notification sound, or the third notification sound based on the input notification sound information.

Here, the first notification sound may contain the first low-pitched note and the first high-pitched note, the second notification sound may contain the second low-pitched note and the second high-pitched note, and the third notification sound may contain the third low-pitched note and the third high-pitched note. That is, each of the first notification sound, the second notification sound, and the third notification sound contains two or more notes.

Here, the notes with different pitches contained in each of the first notification sound, the second notification sound, and the third notification sound may be designed such that a different number of notes with different pitches are emitted according to the magnitude of the acting force.

Specifically, the first notification sound to be emitted when the magnitude of the acting force is less than the first threshold may be designed such that the number of the notes forming the first notification sound is increased as the magnitude of the acting force becomes larger. More specifically, a configuration may be adopted in which, when the magnitude of the acting force reaches or exceeds a certain magnitude less than the first threshold, a note pitched differently from the first low-pitched note and the first high-pitched note is further added to the first notification sound containing the first low-pitched note and the first high-pitched note, thus allowing the first notification sound to contain the three notes with different pitches. When the magnitude of the acting force becomes even larger to be a certain magnitude or larger, a note pitched differently from the notes contained in the first notification sound may be further added, thus allowing the first notification sound to contain the four notes with different pitches.

Such a configuration makes it possible to recognize the difference in the magnitude of the acting force in more detail. Specifically, when the acting force with the magnitude less than the first threshold is applied, the magnitude of the applied acting force can be recognized through the number of the notes with different pitches contained in the first notification sound.

Although the cases where the number of the notes with different pitches contained in the first notification sound is three and four have been described, the number of the notes with different pitches forming the first notification sound may be five or more.

Similarly, the second notification sound to be emitted when the magnitude of the acting force is larger than or equal to the first threshold and less than the second threshold may be designed such that the number of the notes contained in the second notification sound is increased as the magnitude of the acting force becomes larger. Specifically, a configuration may be adopted in which, when the magnitude of the acting force reaches or exceeds a certain magnitude larger than or equal to the first threshold and less than the second threshold, a note pitched differently from the second low-pitched note and the second high-pitched note is further added to the second notification sound containing the second low-pitched note and the second high-pitched note, thus allowing the second notification sound to contain the three notes with different pitches. When the magnitude of the acting force becomes even larger to be a certain magnitude or larger, a note pitched differently from the notes contained in the second notification sound may be further added, thus allowing the second notification sound to contain the four notes with different pitches.

Such a configuration makes it possible to recognize the difference in the magnitude of the acting force in more detail. Specifically, when the acting force with the magnitude larger than or equal to the first threshold and less than the second threshold is applied, the magnitude of the applied acting force can be recognized through the number of the notes with different pitches contained in the second notification sound.

Similarly, the third notification sound to be emitted when the magnitude of the acting force is larger than or equal to the second threshold may be designed such that the number of the notes contained in the third notification sound is increased as the magnitude of the acting force becomes larger. Specifically, a configuration may be adopted in which, when the magnitude of the acting force reaches or exceeds a certain magnitude larger than or equal to the second threshold, a note pitched differently from the third low-pitched note and the third high-pitched note is further added to the third notification sound containing the third low-pitched note and the third high-pitched note, thus allowing the third notification sound to contain the three notes with different pitches. When the magnitude of the acting force becomes even larger to be a certain magnitude or larger, a note pitched differently from the notes contained in the third notification sound may be further added, thus allowing the third notification sound to contain the four notes with different pitches.

Such a configuration makes it possible to recognize the difference in the magnitude of the acting force in more detail. Specifically, when the acting force with the magnitude larger than or equal to the second threshold is applied, the magnitude of the applied acting force can be recognized through the number of the notes with pitches contained in the third notification sound.

For example, it is possible to make a hearer aware that the degree of abnormality is great through the increase in the number of the notes with different pitches contained in the third notification sound as a result of the magnitude of the acting force being far beyond the second threshold.

There may be two or more combinations of the two or more notes contained in each of the first notification sound, the second notification sound, and the third notification sound. Taking the first notification sound as an example for explanation, separately from the combination of the first low-pitched note and the first high-pitched note, another combination of two or more notes with different pitches may be included in the first notification sound. Such another combination of two or more notes with different pitches may be a combination of notes pitched to be consonant with each other. Specifically, such another combination of two or more notes with different pitches may be a seventh chord, or may be another chord, such as a triad.

Here, each of the two or more combinations of the two or more notes with different pitches included in each of the first notification sound, the second notification sound, and the third notification sound may be associated with the magnitude of the acting force.

Specifically, in a case where the first notification sound includes two or more combinations of the two or more notes with different pitches and where one of the two or more combinations is referred to as a first combination and a combination different from the first combination is referred to as a second combination, when an acting force with less than a specified magnitude less than the first threshold is generated, a sound of the first combination may be emitted as the first notification sound, and when an acting force with the specified magnitude or larger, which is less than the first threshold, is generated, a sound of the second combination may be emitted as the first notification sound.

The two or more combinations included in the first notification sound are not limited to the first combination and the second combination, and three or more combinations may be set.

In some embodiments, a configuration may be adopted in which, as the magnitude of the acting force becomes larger, a combination of notes felt more dissonant is emitted as the first notification sound. For example, in some embodiments, a configuration may be adopted in which, as the strength of the acting force becomes larger, the combination of notes included in the first notification sound is changed from a combination of notes including a consonance to a combination of notes dissonant with each other. In some embodiments, a configuration may be adopted in which, as the strength of the acting force becomes larger, the combination of notes included in the first notification sound may be changed sequentially so as to be a combination for a perfect consonance, a combination for an imperfect consonance, and a combination for a sound other than a consonance.

In a case where the second notification sound includes two or more combinations of the two or more notes with different pitches and where one of the two or more combinations is referred to as a first combination and a combination different from the first combination is referred to as a second combination, when an acting force with less than a specified magnitude larger than or equal to the first threshold and less than the second threshold is generated, a sound of the first combination may be emitted as the second notification sound, and when an acting force with the specified magnitude or larger, which is larger than or equal to the first threshold and less than the second threshold, is generated, a sound of the second combination may be emitted as the second notification sound.

The two or more combinations included in the second notification sound are not limited to the first combination and the second combination, and three or more combinations may be set.

In some embodiments, a configuration may be adopted in which, as the magnitude of the acting force becomes larger, a combination of notes felt more dissonant is emitted as the second notification sound. In some embodiments, a configuration may be adopted in which, as the strength of the acting force becomes larger, the combination of notes included in the second notification sound is changed from a combination of notes including a consonance to a combination of notes dissonant with each other. In some embodiments, as the strength of the acting force becomes larger, the combination of notes included in the second notification sound may be changed sequentially so as to be a combination for a perfect consonance, a combination for an imperfect consonance, and a combination for a sound other than a consonance.

In a case where the third notification sound includes two or more combinations of the two or more notes with different pitches and where one of the two or more combinations is referred to as a first combination and a combination different from the first combination is referred to as a second combination, when an acting force with less than a specified magnitude larger than or equal to the second threshold is generated, a sound of the first combination may be emitted as the third notification sound, and when an acting force with the specified magnitude or larger, which is larger than or equal to the second threshold, is generated, a sound of the second combination may be emitted as the third notification sound.

The two or more combinations included in the second notification sound are not limited to the first combination and the second combination, and three or more combinations may be set.

In some embodiments, a configuration may be adopted in which, as the magnitude of the acting force becomes larger, a combination of notes felt more dissonant is emitted as the third notification sound. In some embodiments, as the strength of the force becomes larger, the combination may be changed so as to be a combination with a larger number of notes for a sound other than a consonance being included in the third notification sound.

Some embodiments include the first notification sound to be emitted when the magnitude of the acting force is small, the second notification sound to be emitted when the magnitude of the acting force is large, and the third notification sound to be emitted when the magnitude of the acting force is beyond the range anticipated in advance and an abnormality is considered to have occurred.

Here, the largeness/smallness of the volumes of the first notification sound and the second notification sound may be designed to be that corresponding to the magnitude of the acting force.

Specifically, the volume of the first notification sound to be emitted when the magnitude of the acting force is less than the first threshold may be designed to be increased as the magnitude of the acting force becomes larger.

Also, the volume of the second notification sound to be emitted when the magnitude of the acting force is larger than or equal to the first threshold and less than the second threshold may be designed to be increased as the magnitude of the acting force becomes larger.

Such a configuration makes it possible to recognize the difference in the magnitude of the acting force in more detail. Specifically, when the acting force with the magnitude smaller than the first threshold or the second threshold is applied, the magnitude of the applied acting force can be recognized through the largeness/smallness of the sound volumes.

The strength/weakness, in other words the largeness/smallness of the volume, of the third notification sound may be designed to be that corresponding to the magnitude of the acting force.

With such a configuration, when the magnitude of the acting force is beyond the range anticipated in advance and an abnormality is considered to have occurred, that is, when the magnitude of the acting force is larger than or equal to the second threshold, the degree of abnormality in the magnitude of the acting force can be recognized through the largeness/smallness of the sound volume.

For example, it is possible to make a hearer aware that the degree of abnormality is great by the relatively large third notification sound being emitted as a result of the magnitude of the acting force being far beyond the second threshold.

A fourth notification sound may be further provided that is a notification sound other than the first notification sound, the second notification sound, and the third notification sound having the respective functions described above. Similarly, a fifth notification sound and the subsequent notification sounds may be provided.

In some embodiments, the first high-pitched note is consonant with the first low-pitched note, and the second high-pitched note is consonant with the second low-pitched note.

However, the first high-pitched note is not limited to a note consonant with the first low-pitched note, and the second high-pitched note is not limited to a note consonant with the second low-pitched note. For example, the first high-pitched note does not have to be consonant with the first low-pitched note, that is, may be dissonant with the first low-pitched note, and the second high-pitched note does not have to be consonant with the second low-pitched note, that is, may be dissonant with the second low-pitched note.

The technical scope of the present disclosure is not limited to the above-described embodiments, and various modifications can be made within the scope not departing from the gist of the present disclosure. For example, the technical scope is not limited to that in which the present disclosure is applied to each of the respective modes of the first notification sound, the second notification sound, and the third notification sound described above, and these modes may be combined as appropriate, thus placing no particular limitation.

It is to be understood that the present disclosure is not limited to the above embodiments, but various changes and modifications may be made therein without departing from the spirit and scope thereof as set forth in appended claims.

What is claimed is:

1. A force sense notification device comprising a control device configured to implement at least:
    an input part which receives a measurement signal indicating a magnitude of an acting force exerted on a surgical instrument;
    a sound information generator configured to generate, based on the measurement signal, notification sound information indicating the magnitude of the acting force; and
    an outputter configured to output the notification sound information generated by the sound information generator to a sound generator configured to emit a sound based on the notification sound information,
    wherein the notification sound information comprises:
        a first notification sound having a first low-pitched note and a first high-pitched note pitched higher than the first low-pitched note, and
        a second notification sound having a second low-pitched note and a second high-pitched note pitched higher than the second low-pitched note, at least one of the second low-pitched note or the second high-pitched note being different in pitch from the first low-pitched note and being different in pitch from the first high-pitched note, and
    wherein the first low-pitched note and the second low-pitched note are repeatedly changed in loudness, or the first high-pitched note and the second high-pitched note are repeatedly changed in loudness.

2. The force sense notification device according to claim 1, wherein:
    the first high-pitched note is consonant with the first low-pitched note.

3. The force sense notification device according to claim 2, wherein:
    the second high-pitched note is consonant with the second low-pitched note.

4. The force sense notification device according to claim 1, wherein:
    the second high-pitched note is consonant with the second low-pitched note.

5. The force sense notification device according to claim 1, wherein:
    at least one of the first notification sound or the second notification sound contains two or more notes different in pitch from each other, the two or more notes different in pitch being notes pitched to be consonant with each other.

6. The force sense notification device according to claim 1, wherein:
    the second low-pitched note is pitched higher than the first low-pitched note, and the second high-pitched note is pitched higher than the first high-pitched note.

7. The force sense notification device according to claim 1, wherein:
a pace of the repeated changes in loudness of the second notification sound is different from a pace of the repeated changes in loudness of the first notification sound.

8. The force sense notification device according to claim 1, wherein:
the first high-pitched note and the second high-pitched note are notes a seventh above the first low-pitched note and the second low-pitched note, respectively.

9. The force sense notification device according to claim 1, wherein:
the sound information generator is configured to, when the magnitude of the acting force is larger than or equal to a specified threshold, generate the notification sound information indicating that the magnitude of the acting force is larger than or equal to the specified threshold, and
wherein the notification sound information comprises a third notification sound that is different from the first notification sound and the second notification sound and that indicates the magnitude is larger than or equal to the specified threshold.

10. The force sense notification device according to claim 9, wherein:
the third notification sound comprises a third low-pitched note and a third high-pitched note pitched higher than the third low-pitched note, and
the third low-pitched note and the third high-pitched note are dissonant with each other.

11. The force sense notification device according to claim 9, wherein:
the third notification sound comprises a third low-pitched note, a third middle-pitched note pitched higher than the third low-pitched note, and a third high-pitched note pitched higher than the third middle-pitched note, and
one note of the third low-pitched note, the third middle-pitched note, and the third high-pitched note is emitted continuously, and the remaining two notes are emitted alternately.

12. The force sense notification device according to claim 1, wherein:
the sound information generator is configured to, when the magnitude of the acting force is larger than or equal to a specified threshold, generate the notification sound information indicating that the magnitude of the acting force is larger than or equal to the specified threshold.

13. The force sense notification device according to claim 1, further comprising:
a switcher configured to permit and prohibit generation of the sound in the sound information generator.

14. The force sense notification device according to claim 1, wherein the control device is further configured to implement:
an image generator that generates image information indicating the magnitude of the acting force, based on the measurement signal, to be presented on a display device.

15. A force sense notification method comprising:
receiving a measurement signal indicating a magnitude of an acting force exerted on a surgical instrument;
generating, based on the measurement signal, notification sound information indicating the magnitude of the acting force; and
outputting the notification sound information to a sound generator configured to emit a sound based on the notification sound information,
wherein the notification sound information comprises:
a first notification sound having a first low-pitched note and a first high-pitched note pitched higher than the first low-pitched note, and
a second notification sound having a second low-pitched note and a second high-pitched note pitched higher than the second low-pitched note, at least one of the second low-pitched note or the second high-pitched note being different in pitch from the first low-pitched note and being different in pitch from the first high-pitched note, and
wherein the first low-pitched note and the second low-pitched note are repeatedly changed in loudness, or the first high-pitched note and the second high-pitched note are repeatedly changed in loudness.

16. A force sense notification device comprising a control device configured to implement at least:
an input part which receives a measurement signal indicating a magnitude of an acting force exerted on a surgical instrument;
a sound information generator configured to generate, based on the measurement signal, notification sound information indicating the magnitude of the acting force; and
an outputter configured to output the notification sound information generated by the sound information generator to a sound generator configured to emit a sound based on the notification sound information,
wherein the notification sound information comprises:
a first notification sound having a first low-pitched note and a first high-pitched note pitched higher than the first low-pitched note, and
a second notification sound having a second low-pitched note and a second high-pitched note pitched higher than the second low-pitched note, at least one of the second low-pitched note or the second high-pitched note being different in pitch from the first low-pitched note and being different in pitch from the first high-pitched note,
wherein the sound information generator is configured to, when the magnitude of the acting force is larger than or equal to a specified threshold, generate the notification sound information indicating that the magnitude of the acting force is larger than or equal to the specified threshold, and
wherein the notification sound information comprises a third notification sound that is different from the first notification sound and the second notification sound and that indicates the magnitude is larger than or equal to the specified threshold.

* * * * *